United States Patent [19]

Daneshvar

[11] Patent Number: 5,644,797
[45] Date of Patent: Jul. 8, 1997

[54] PUNCTURE RESISTANT GLOVES

[76] Inventor: Yousef Daneshvar, 21459 Woodfarm, Northville, Mich. 48167

[21] Appl. No.: 169,497

[22] Filed: Dec. 20, 1993

[51] Int. Cl.$^6$ .................... A41D 13/10; A41D 19/00
[52] U.S. Cl. ................................ 2/161.7; 2/163; 2/21
[58] Field of Search .................... 2/16, 21, 161.6, 2/159, 161.7, 161.8, 163, 168, 160

[56] References Cited

U.S. PATENT DOCUMENTS

| | | | |
|---|---|---|---|
| 183,375 | 10/1876 | Cutliff | 2/161.8 |
| 692,703 | 2/1902 | Pfeiffer, Jr. | 2/168 |
| 1,346,683 | 7/1920 | Reynolds | 2/161.8 |
| 1,911,500 | 5/1933 | Gowdy et al. | 2/161.8 |
| 2,056,413 | 4/1936 | Harbruck | 2/168 |
| 2,847,012 | 8/1958 | Eastman | 2/168 |
| 3,184,756 | 5/1965 | De Luca, Jr. | 2/161.6 |
| 3,283,338 | 11/1966 | Landau | 2/168 |
| 3,290,695 | 12/1966 | Burtoff | 2/161.8 |
| 3,386,104 | 6/1968 | Casey | 2/161.6 |
| 3,732,575 | 5/1973 | Pakulak | 2/161.6 |
| 4,131,952 | 1/1979 | Brenning, Jr. | 2/21 |
| 4,272,849 | 6/1981 | Thurston et al. | 2/161.6 |
| 4,441,213 | 4/1984 | Trumble et al. | 2/163 |
| 4,507,804 | 4/1985 | Consigny | 2/21 |
| 4,681,012 | 7/1987 | Stelma et al. | 2/163 |
| 4,845,780 | 7/1989 | Reimers et al. | 2/161.7 |
| 4,858,245 | 8/1989 | Sullivan et al. | 2/21 |
| 4,867,246 | 9/1989 | Kiger | 2/161.8 |
| 5,093,933 | 3/1992 | Berry | 2/163 |
| 5,173,966 | 12/1992 | Delco | 2/168 |
| 5,259,069 | 11/1993 | Gimbel | 2/168 |
| 5,323,490 | 6/1994 | Yarbrough | 2/161.7 |

FOREIGN PATENT DOCUMENTS

| | | | |
|---|---|---|---|
| 2448307 | 9/1980 | France | 2/161.8 |
| 2686013 | 7/1993 | France | 2/161.7 |
| 809741 | 3/1959 | United Kingdom | 2/168 |
| 9013232 | 11/1990 | WIPO | 2/168 |

*Primary Examiner*—Amy B. Vanatta

[57] ABSTRACT

A puncture resistant glove is shown which includes a puncture resistant layer disposed on non-puncture resistant portions for protection of a wearer's digits. The puncture resistant layer includes a series of shields of puncture resistant material which overlap at the joints to protect the joint, but allow flexing of the joint. The glove may also include accordion-shaped zones which allow easier flexing and extension of the glove. The resulting glove provides protection for the hand while maintaining a good fit and being comfortable.

8 Claims, 13 Drawing Sheets

PUNCTURE RESISTANT GLOVES

THE BACKGROUND OF THE INVENTION

Gloves have been used for a very long time, however there has been problems with their use which is much more noticeable now, when the need for their use and protection is more. The introduction of HIV virus has created, a great many new concerns, one of them is prevention of being stuck by a contaminated needle and sharp object, and this is a great problem in the medical field; from assisting in operation to gathering and cleaning the contaminated materials, all brings the fear and possibility of being stuck by a contaminated needle and a sharp object and there has been no solution that the inventor knows of. Double gloving has not been an answer when a sharp needle can easily go through the thickness of it when stuck in the right angle. Considering these problems it should be noted that in general the protective gloves are not comfortable and many of them are so bulky and disturbing that some people stop using them. Therefore the inventor is introducing his own ideas in this regard having the hope that these new units help many human beings. The advantages of these new units can be used in medicine as well as general use.

BRIEF EXPLANATION OF INVENTION

This invention deals with making a special glove that will be made with a design and components to make them better and more comfortable units. Although many materials may be used for constructing these units, the main models of these new units will be made from latex, and a design and improvements will be used to make better and more comfortable and efficient units. Also some models of these gloves will be made to have a series of hard protective plastic or metal on or inside its wall or under its inner surface or in any part of its thickness or surfaces to prevent from the sharp objects from perforating the whole thickness of this unit and prevent the problem of being poked by sharp objects to some degree. It is true that this technique will cause some difficulty however at least it could be used in certain cases. The special shape of the surface of these gloves is believed to be a great improvement and is to give a better grip to the users and allow them to enjoy it more. The shape of protective parts are changed to give more protection as well.

THE DETAILED EXPLANATION OF THE FIGURES

Figure 1:
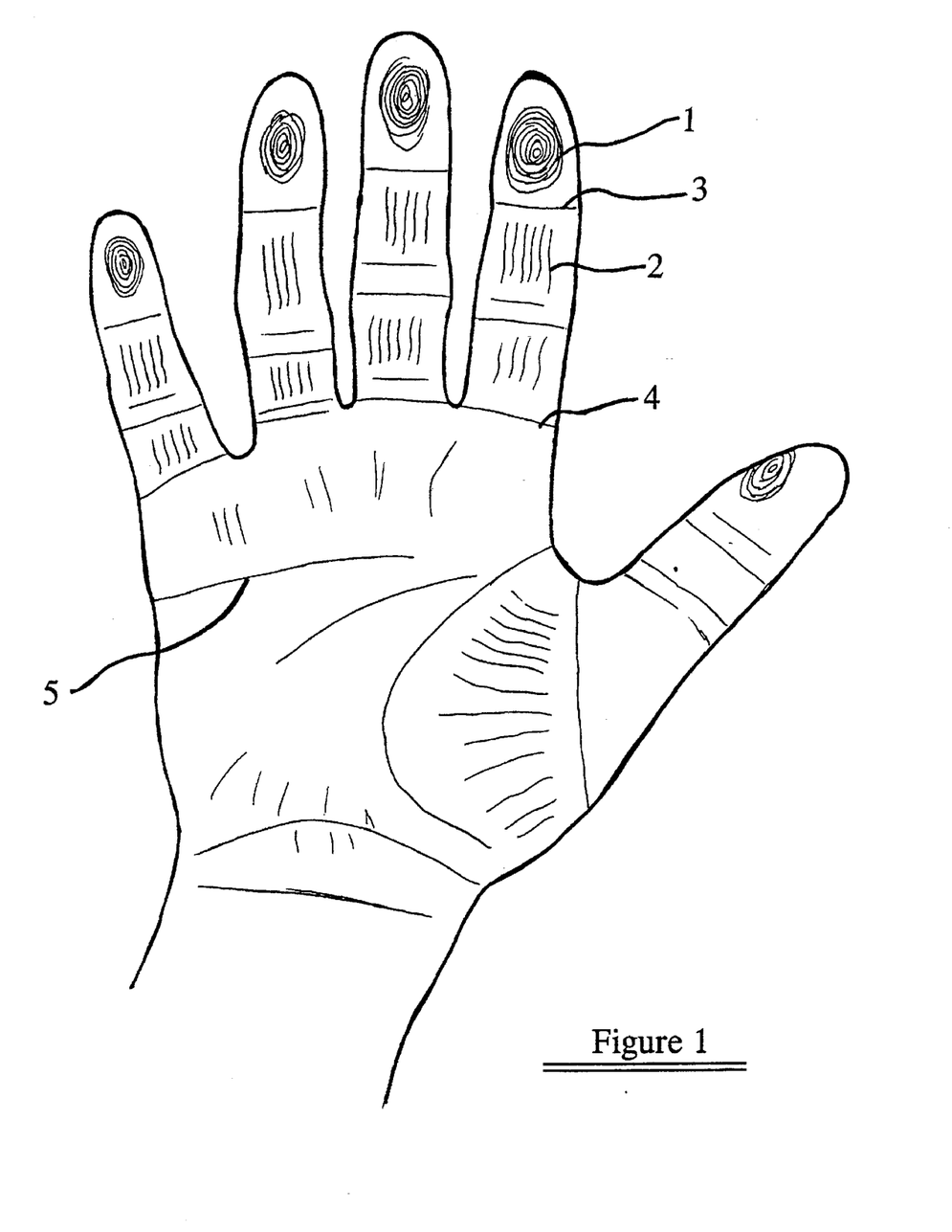
FIG. 1. This figure shows the palm view of a glove that has a series of fine elevated lines of latex on it.

FIG. 1. This figure shows the palm view of a glove that has a series of fine elevated lines of latex simulating the general shape of the lines of a human hand. In this figure the raised lines in the tip of the 2nd finger is shown at 1, the longitudinal lines in the same finger by 2 and 3 and 4 show lines that will be over the joint and may have a line of depression or a thinner line in order to allow the wall of the glove to be bent along that line easily. The same may be true about the line 5 and similar lines as well.

Figure 2:
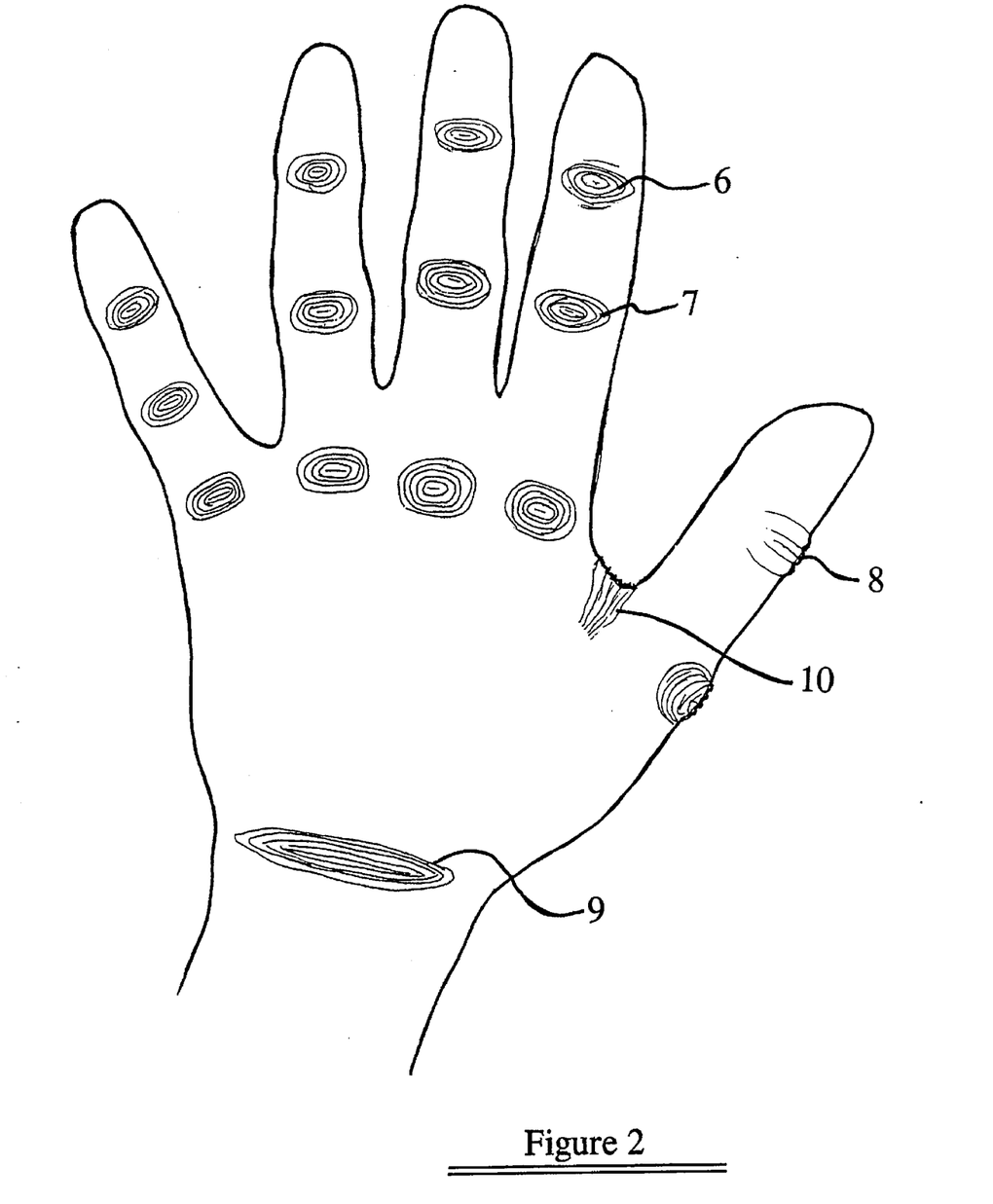
FIG. 2. This figure shows the rear surface of a glove that has extra skin over the knuckles.

FIG. 2. This figure shows the general view of the rear surface of a glove that has areas of extra skin proximate the knuckles of the fingers and the other joints of the hands. These areas will have a wall similar to the wall of an accordion in the position of the joint and similar to the skin of a person in that area so that it will allow the skin to expand and shrink easily when the person bends his finger and then straightens it respectively. This method is to prevent the elastic wall of the gloves from pulling a bent finger toward an open position and cause at least an unconscious resistance of the user against it and fatigue. In this figure the areas 6 and 7 are in front of the joints of the second finger and 8 is over the distal joint of the thumb and 9 is over the wrist area, 10 shows the area between the thumb and the second finger. The position and the number of these lines and the size of their areas may vary.

Figure 3:
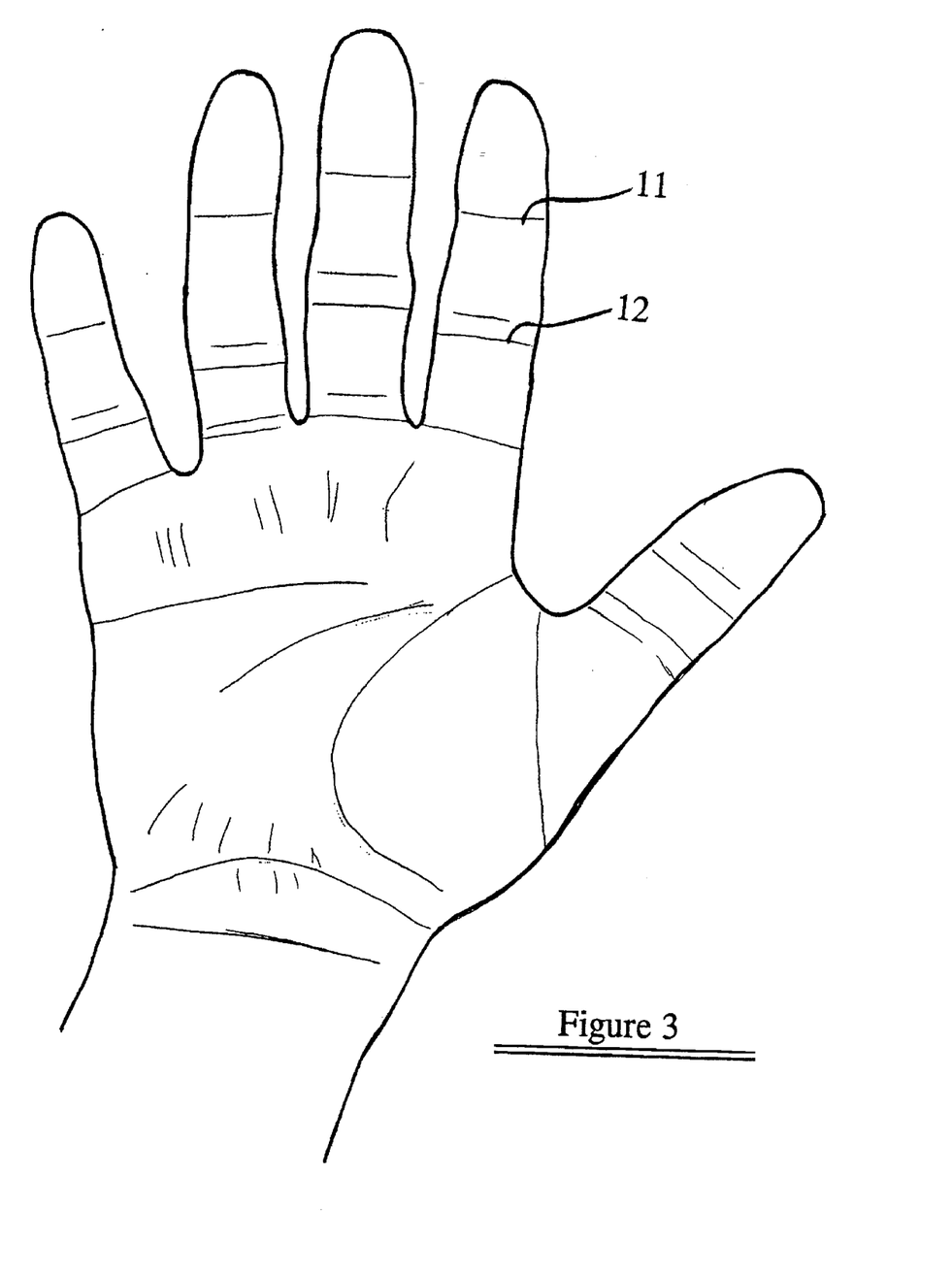
FIG. 3. This figure shows the palm of a glove with lines marked over the natural folding lines of the palms.

FIG. 3. This figure shows the palm side of a glove and the lines marked here are basically over the natural folding lines of the palms over the joints. This figure and lines 11 and 12 (used as examples) are to indicate that the glove may have lines of depression or a thinner wall or line in such areas in order to facilitate and allow the wall of the glove to be bent along that line easily.

Figure 4:
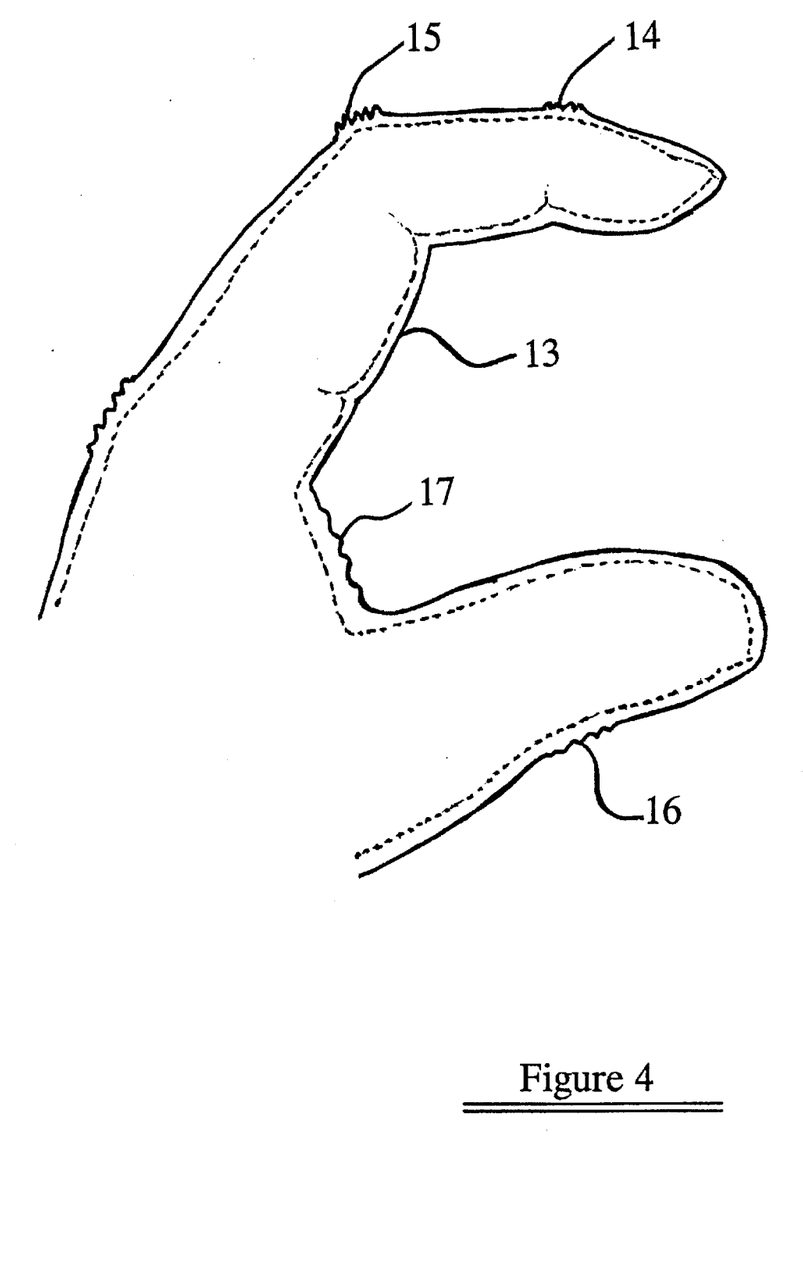
FIG. 4. This figure shows the cross cut of a part of hand wearing a glove.

FIG. 4. This figure shows schematically the cross cut of a part of a hand, the second finger and the thumb that is wearing a glove. This view is especially to show the side view of the glove over the knuckles and the extra wall over them which has a zig-zag shape or similar to wall of an accordion. This part will be made to have a larger area to allow expansion area and a low resistance against expansion and retraction. In this figure the wall of the glove is shown at 13 and the extra wall in the 2nd finger is marked at 14 & 15 and in one joint of the thumb at 16 and between the base of the thumb and the second finger at 17.

Figure 5:
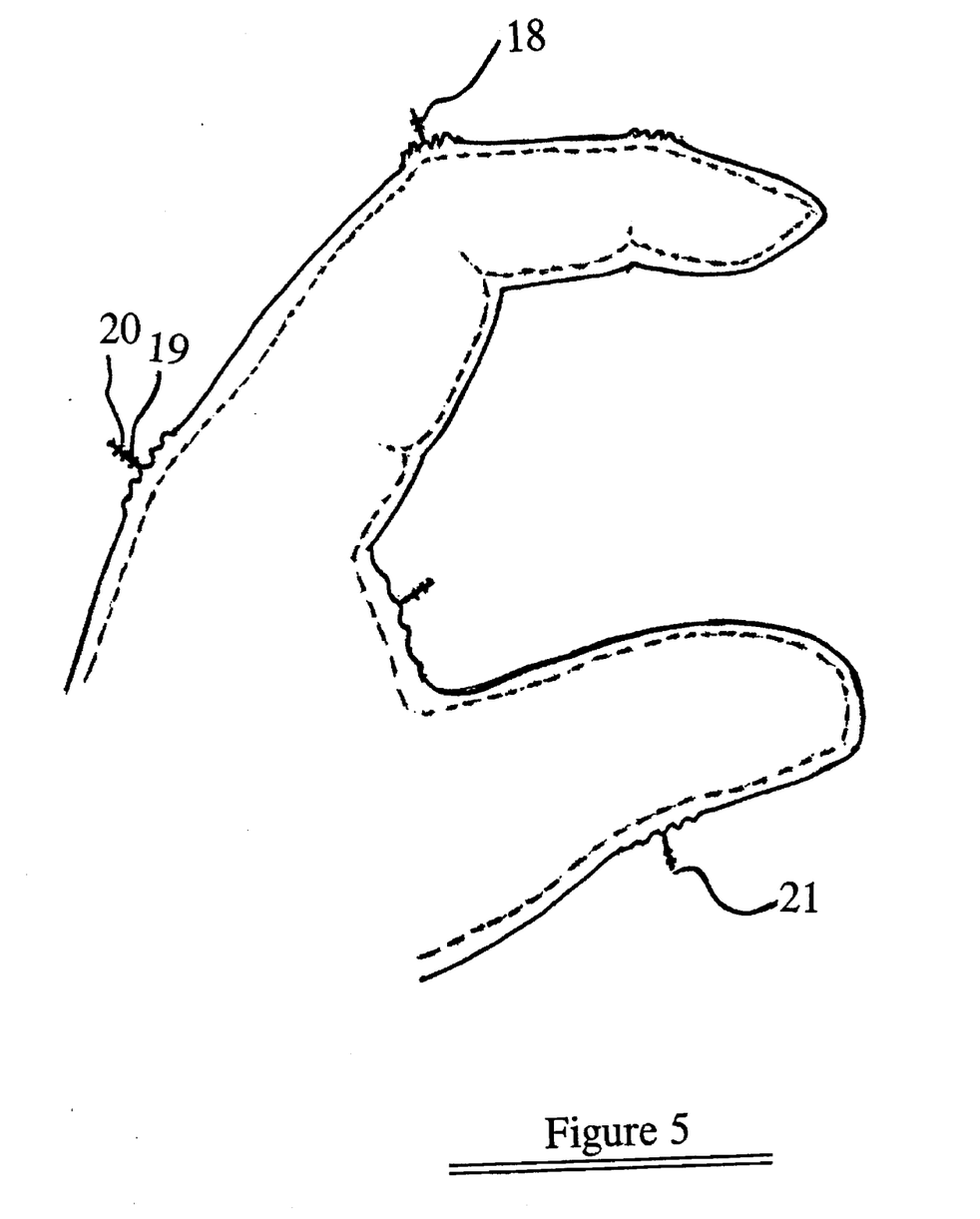
FIG. 5. This figure shows the surface of a glove with number of tabs on its knuckles.

FIG. 5. This figure shows a glove similar to one shown in previous FIG. 4, except this figure shows that the surface of this glove may have a number of tabs in certain spots that are to allow the wall of the glove to be pulled easily and positioned without a need for pinching the wall of the glove to perforate or weaken it. In this figure one such tab is shown at 18 over the joint of the second finger, the other one at 19 and 21. 20 is to show that the surface of this tab may have fine raised spots or lines to allow a better grip.

Figure 6:
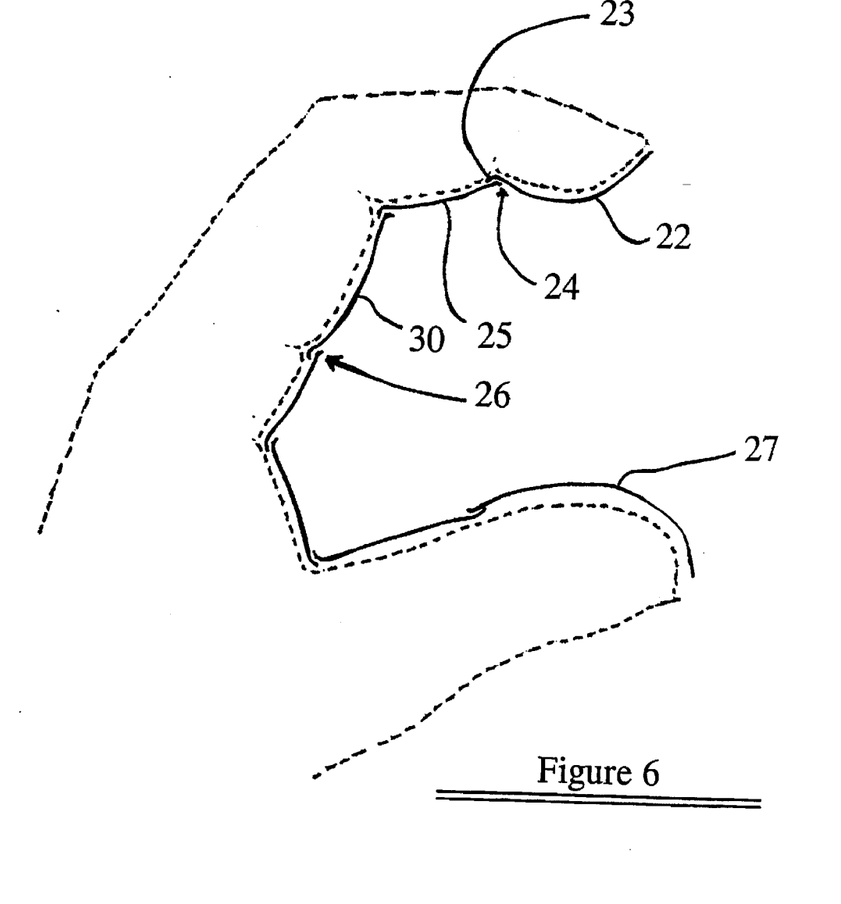
FIG. 6. This figure shows schematically a hand drawn in a dotted line with a series of shields on it.

FIG. 6. This figure shows schematically a hand drawn in dotted lines with a series of shields on it. The shields will be made from protective materials in a shape to stand over the parts of the hands and fingers to prevent from trans passing a sharp object. The actual thickness of the shield may be thicker than one shown in this figure. These shields will match and fit the fingers and different areas of the hands to function easily. Also they will be made to have a rim in the joint area to prevent the tip of sharp objects to slide and go to an unprotected area of skin.

These rims may be also made in the edges of these shields as well. In the joint areas of the fingers the connection parts of these shields will have a function of preventing creation of empty space by having the edge of one shield overlap and go over the other one and to make a joint type connection, and provide a better protection. In this figure the shield on the tip of the second finger is shown at 22 with its proximal end at 23 forming a shallow trough the distal tip of the shield 25 is shown at 24 which is overlapping and standing on the small sharp angulation of the proximal end of the shield 22, which is in the connection line between the body and end of (23) piece 22. Then the shield 30 is shown with the tip of the proximal shield before that overlapping it at 26. The shield over the thumb is shown at 27.

Figure 6A:
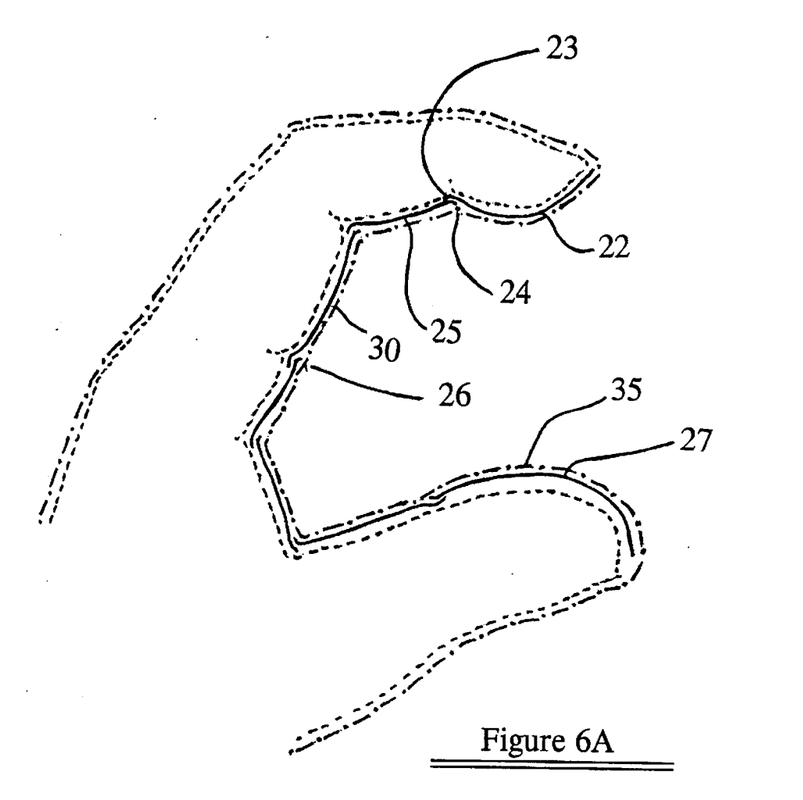
FIG. 6A. This is similar to previous FIG. 6 except in this figure the body of the glove is also shown.

FIG. 6A. This figure is basically similar to previous FIG. 6 except in this figure the body of the glove made from an elastic material is also shown at 35 which goes over the hand and the protective shields as well.

Figure 6B:
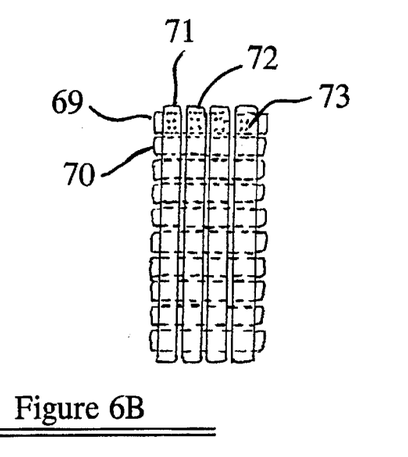
FIG. 6B. This shows combinations of a series of steels to provide the protection.

FIG. 6B. This figure shows a series of steel bands which are combined with each other to make a shield for prevention of penetration of the sharp objects. These can be placed inside the wall of the latex glove or in its vicinity in order to function as planned. Importantly the layers may be more than two to make the protection more. In this figure two of the longitudinal steel bands are marked at 71 and 72 and two of the horizontal steel bands are shown at 69 and 70. The surface of these bands may have lines and rough surface to prevent slipping of the tip of sharp objects. The shape and size and other important characteristics of these bands may vary.

Figure 6C:
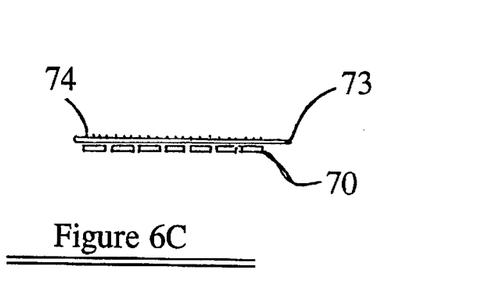
FIG. 6C. This shows the side view of the unit shown in previous figure.

FIG. 6C. This figure shows a side view of the protective shield shown in previous FIG. 6B. In this figure one longitudinal steel band is marked at 73 with its rough surface shown at 74 and the cuts of one horizontal steel band is shown at 70. The surface of these bands may have lines and a rough surface to prevent slipping of the tip of sharp objects.

Figure 7:
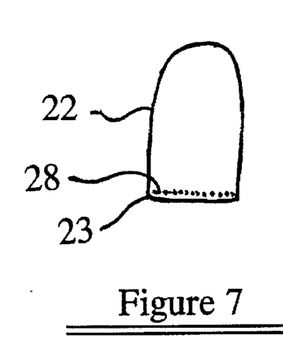
FIG. 7. This shows a general view of a shield shown in previous FIG. 6, at the tip of the second finger.

FIG. 7. This figure shows a general view of one shield that was shown in previous FIG. 6 at the tip of the second finger. This shield has a body shown at 22 and the proximal end of it shown at 23 is connected to the body at an angulated line shown at dotted line 28. There is a depressed line along this line 28 and this is intended to prevent the slipping motion of the tip of a sharp object to continue and reach an unprotected area of the skin.

Figures 8, 9:
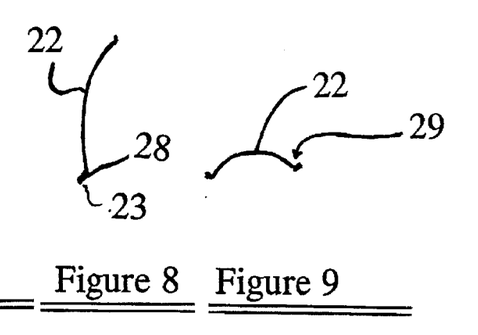
FIG. 8. This figure shows a longitudinal side view cut of the shield shown in previous FIG. 7.
FIG. 9. This shows a horizontal cross cut of the shield shown in previous FIG. 7.

FIG. 8. This figure shows a longitudinal side view cut of the shield shown in previous FIG. 7. This shows the body 22 and the proximal end of it shown at 23 and the tip of angulated line 28.

FIG. 9. This figure shows a horizontal cross cut of the shield shown in previous FIG. 7. This shows the curve of the body 22 that will fit the curve of the finger and in the side it has a narrow depression shown in one side at 29. This is to stop the motion of the tip of the sharp object at this spot and prevent it from reaching the unprotected area, although some embodiments may not have it. The surface of these shields may not be soft either and they may have lines to prevent a sharp object from sliding easily.

Figure 10:
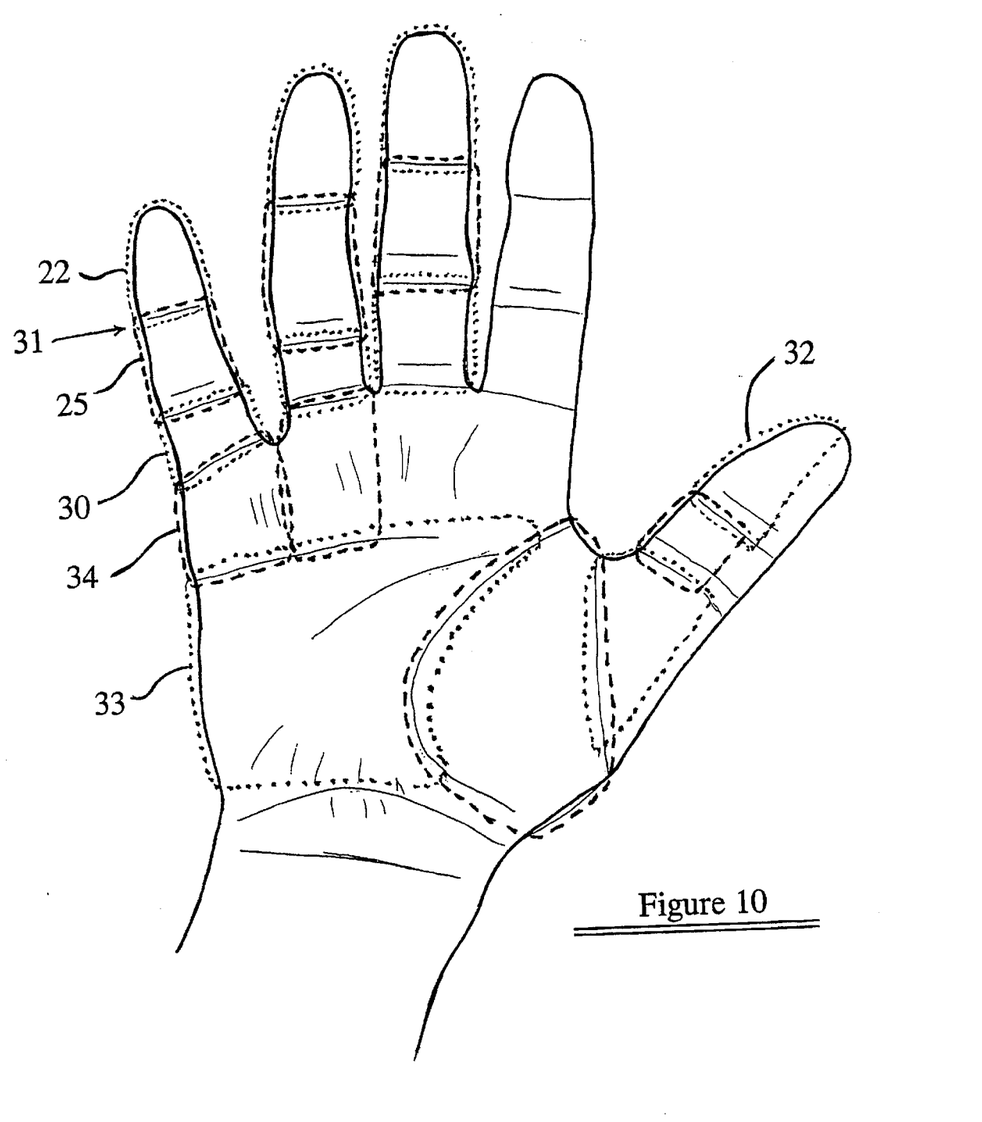
FIG. 10. This shows the palm of a person covered by a series of shields, where their ends overlaps one over another.

FIG. 10. This figure is a schematical view of the palm of a person covered by a series of shields. Their ends overlap one over another to make mosaics of shields. In this figure in order to allow distinction of the borders of the shields one of them is shown by a dotted line while the other one next to it by a broken line. It also is to be noted that the ends of these shields overlap one over another to prevent the presence of an open space. In this figure the shield that covers the tip of the small finger is shown at 22 and the one before it at 25 and the line of overlap by 31. The shield before 25 is shown at 30 and one before it at 34. The rest of the shields are not shown to prevent crowding of the picture. However, a few are shown; one at the tip of the thumb at 323 and another one at the base of the hand at 33.

Figure 11:
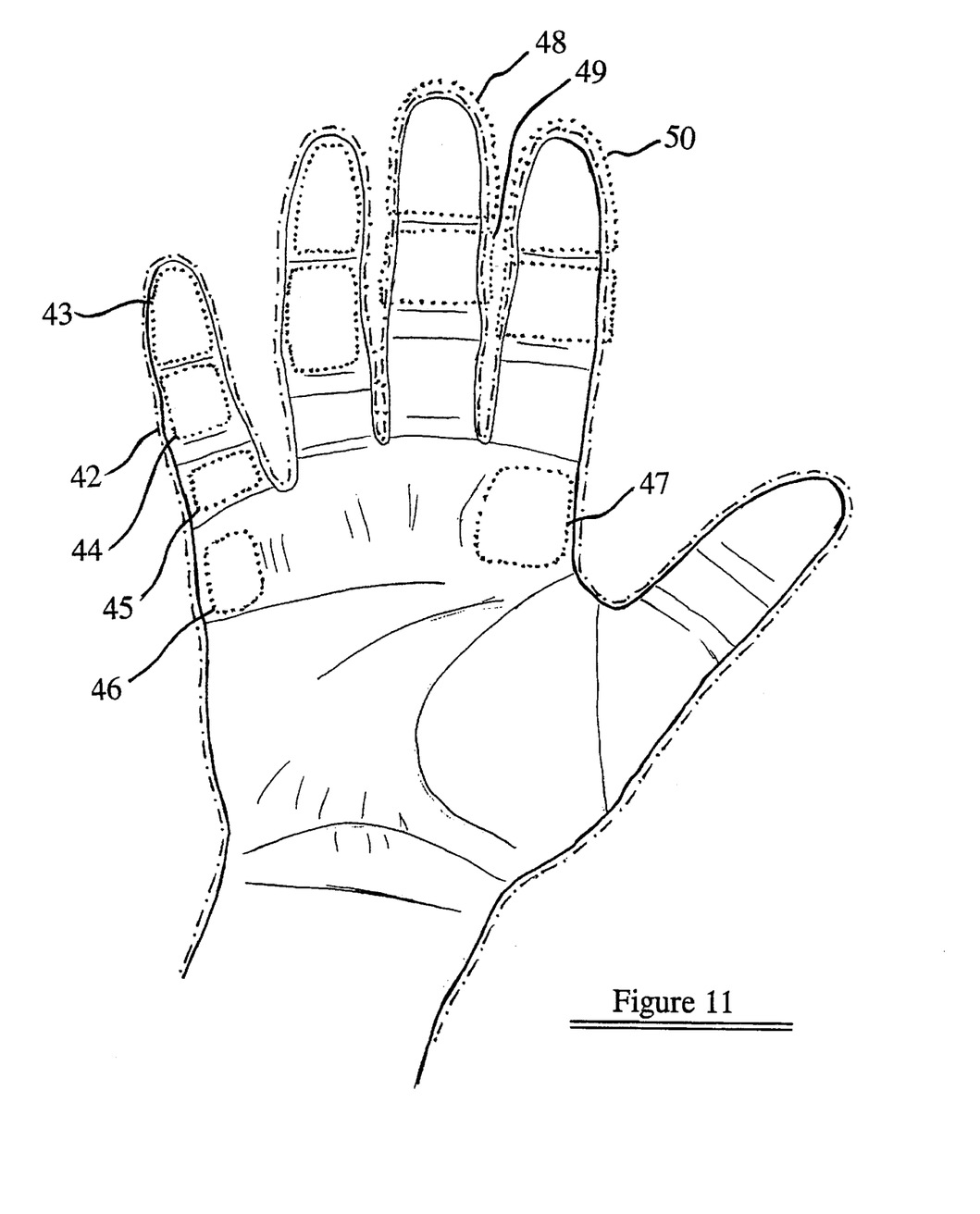
FIG. 11. This is similar to previous FIG. 10. except it shows the body of glove at 42 and protective shields made from a series of patches.

FIG. 11. This figure is basically very similar to the one shown in previous FIG. 10, except for two main differences: First, this figure shows the hand which is now covered by the body of the glove shown at 42 and with a line made with a dot and dash. Second, the protective shields here are made from a series of patches (that can be from the same matrix as the body of the glove or another kind of material) that are stuck to the palm surface of the body of the glove (they may be also stuck to the rear side as well if necessary). Some of these shields are shown at 43, 44, 45, 46, 47. These shields can be of different shapes, sizes and consistencies, etc. For example, the few of them shown at 48, 49 and 50 are larger than the previous patches and go over the front surface of fingers and to the sides as well to cover more area.

Figure 12:
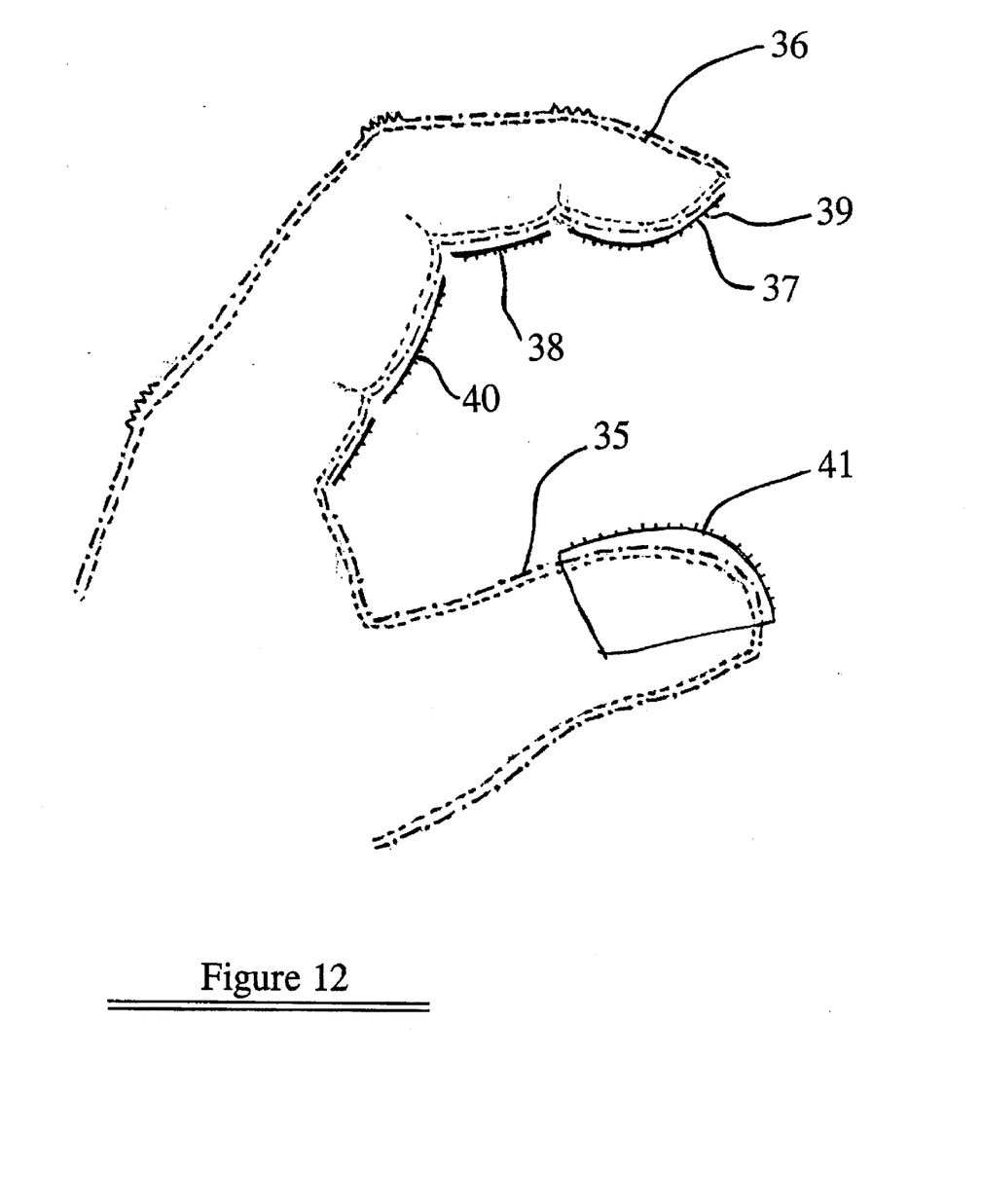
FIG. 12. This shows the side view of a series of the shields shown in previous FIG. 11.

FIG. 12. This figure shows the side view of a series of the shields that are similar to one shown in previous FIG. 11. In this figure, the skin of the hand is shown at 36 in a dotted line. The body of the glove is shown at 35 with a line made with a dot and dash. The cross cut of the protective shields show that they are thicker to be more protective and have a surface that has lines or spots of raised matrix to make them have a better grip. A few of these shields are shown at 37, 38, 40 and 41. The cut of a raised line is shown at 39.

Figure 12A:
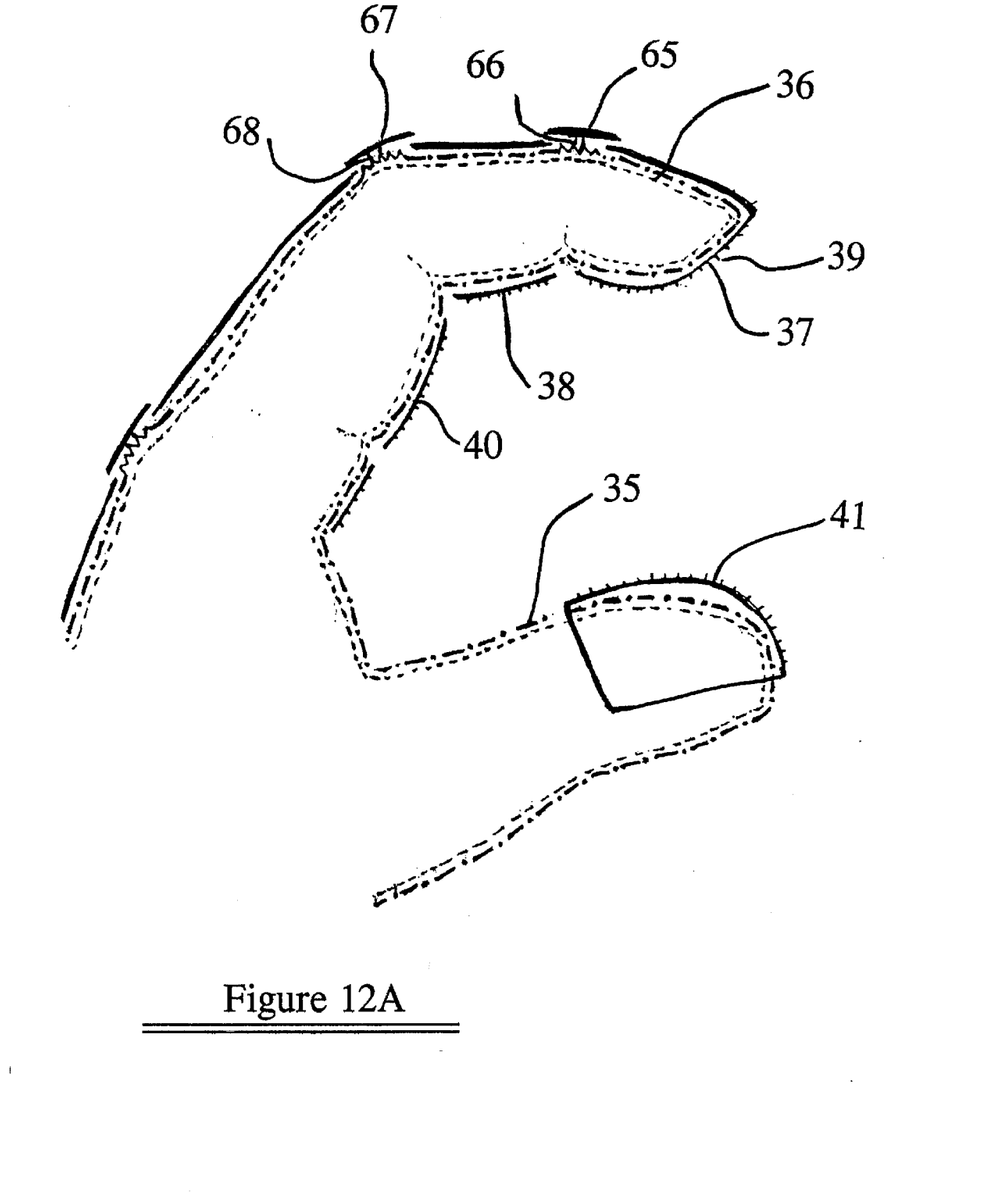
FIG. 12A. This shows a shield in the knuckle area at 65 and 67.

FIG. 12A. This figure is very similar to the previous FIG. 12; except the unit shown in this figure has also a protective shield in the rear surface of the hand, and the rear surface of the glove over the knuckles has a small shield of its own (shown at 65 and 67 as examples) to prevent injury. This shield is connected in some spots (66 and 68 as examples) to the glove in this area.

Figure 13:
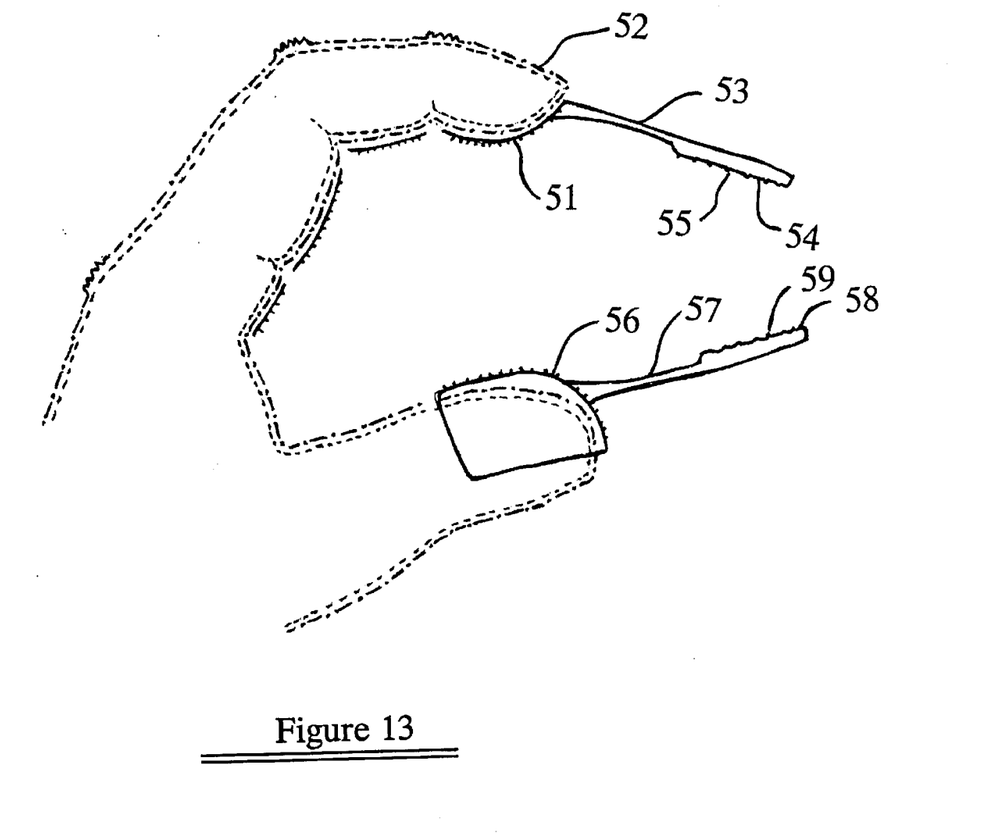
FIG. 13. This shows a protective gloves with a protective part which has extensions in the tip of the fingers.

FIG. 13. This figure shows a different kind of the protective gloves in which the protective part has extensions in the tip of the fingers so that it will prevent the fingers from coming directly in contact with certain hazardous materials, in order to make the chance of contamination or injury significantly remote. For example, with such a unit someone may pick up hot stuff from the surface of a tray without getting burned. Certain chemicals, or a sharp object which has many tips that at least one of which may stick the hands can be picked up without fear of being poked, etc. In this figure, the body of glove the is shown at 52 with a line made of dots and dashes. The cross cut of the protective shield at the tip of the second finger is shown at 51 which has an extension shown at 53 that has an end which is like a small paddle marked at 54. The surface of this paddle has a series of lines or dots to give a better grip and one of them is shown at 55. The tip of the thumb has a similar unit as well, shown at 56, with its extension shown at 57 and the paddle at 58, and the raised part at 59.

Figure 14:
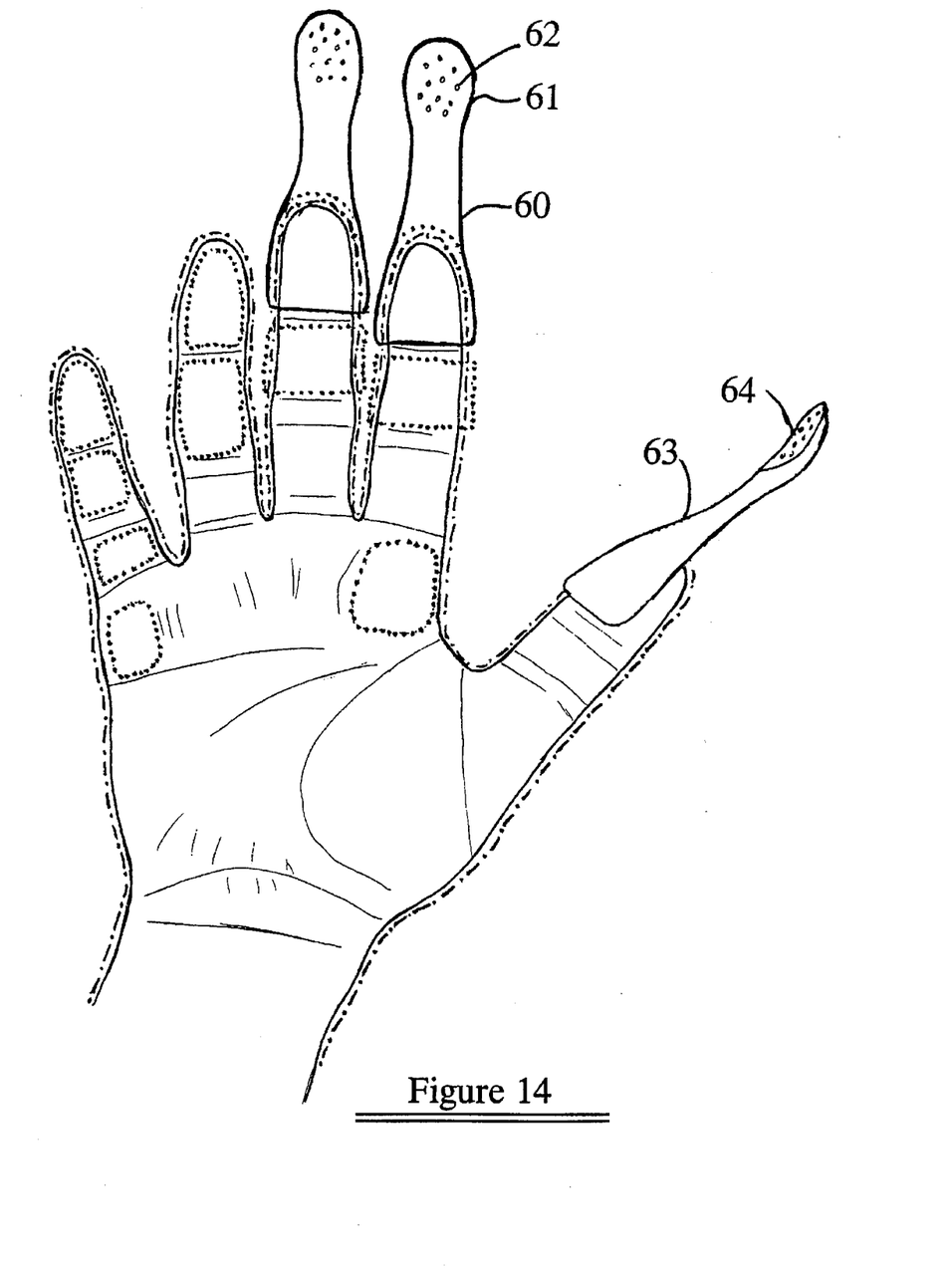
FIG. 14. This figure shows the front view of a unit similar to one shown at previous FIG. 13.

FIG. 14. This figure shows the front view of a unit similar to one shown in previous FIG. 13, except in this unit the shape of the extensions are somewhat different and the tip of the extension in the thumb is shown as a concave surface covered by spots of soft material to increase the grip. The main figure of the extensions in the second and third fingers are shown as well. The size, shape and other characteristics of these pieces will vary in different models, for example the tip of the units may be made to have magnetic pieces to attract some pieces such as needles. This will be of use when a person is cleaning the surgical materials that have contaminated needles scattered in the mixture of many things. Some other models for different uses may be made as well. The materials used in the body of this piece may be different as well, for example when someone uses these units with heated material, the main body of these pieces or some part of them may be made to be non-conductant to heat, or they may be made to be non-conductant to electricity, etc.

THE DETAILED EXPLANATION OF THIS INVENTION

The use of gloves in medicine and in general are long known and part of daily business. They have been used in many professions as well as at home for cleaning, washing dishes, etc. Recently the use of gloves has been particularly stressed in the medical field and the inventor, as a doctor, uses them quite frequently as well. They are protective and useful, however unfortunately there are some problems with use of the present models. One of them is the fact that they are not functional as the human hands and do not grab things as well; this can be felt in cases such as using slippery fine catheters, and rotating them, or using the gloves in similar conditions that precision, as well as better grip and comfort, is required. This is something that this inventor has an idea about it, he believes that one mason that these gloves do not have a better grip is that they do not have a surface in shape of the hands, and god given configurations of the skin of the hands. He believes that if we make a model of gloves that matches the shape of the skin of the hands of human beings to a possible degree, there will be a chance that it will hold the units better and the users such as the inventor will enjoy using them more. For this reason he introduces gloves that have an outer surface which mimics the skin of human hands, for example they will be made to have a series of fine elevated lines of latex that simulates the skin of the hands. Also, some other models will be made with a series of fine elevated spots or raised parts of lines of elevations on it to cause a better grip and act to diminish the discomfort and accidents due to ineffectiveness of such gloves.

The other concern of the inventor has been about the shape and model and construction of these gloves, which in practice and especially after some period of use cause discomfort in the hands of at least certain users so that ideally they wish not to use them if they had the choice. The inventor believes that this is due to a wrong design and importantly the anatomy of the human hands has been ignored. For more explanation it is to be noticed that the latex has a significant degree of elasticity and therefore automatically its pulls the fingers to bring them to its own original shape which was given to it at the time of construction. This pulling effect of the matrix of these gloves has a pulling effect on the fingers and prevents the joints from being kept in bent position easily for a long time, without the user fighting against such movement and the elasticity of the gloves unconsciously, which is naturally an effort and a tiring one. However this inventor has a solution for this problem and what he introduces is to have gloves made with the rear surface of the fingers of these gloves over the joints and even the wrist of the gloves to have an area of extra skin in the shape of a zig-zag or an accordion wall for allowing extension of the wall to be done easily and without much of resistance for a better result. Importantly the material in these areas may be made to be stretchable from two sides that are perpendicular to each other such as making two patterns of accordion perpendicular to each other in one layer, which will allow the layer to be pulled in two perpendicular directions easily (this is not shown in pictures).

Another suggestion of this inventor is about the problem during wearing these gloves, in which many times pulling the gloves on the hands and fingers has to be done by pinching and pulling its wall. This not only is hard but is a wrong technique as well, since sometimes it causes tearing of the wall and is likely to cause weakening of the wall in some cases. To prevent such phenomenon, as well as prevention of contamination which may occur during wearing these gloves, he suggests having "Tabs of Latex", or from the matrix of the glove on the surface of the gloves in different preferred places, to make it able to be pulled easily without having to grab and pinch the wall of the glove for this purpose. These kinds of tabs, or a few larger ones, when placed on the inner surface of the sleeve (when the sleeve of the glove is turned out, as commonly they are packed) will be a means to allow the gloves to be pulled easily and safely over the hands, which some people may like to use.

The other advantage of these gloves will be to have fine lines of the matrix of the gloves in their inner surface, as well to give a better grip and feeling to the user. These lines may be a matching copy of the prominent figures of the hands and fingers of a person or it may consist of raised dots, spots or lines of various patterns, such as parallel, criss crossing, wavy etc. The number, the position, the nature, the size, the shape, the thickness, the length, the width, the coloring, and other important specifics and characteristics of these raised lines or spots may vary from one model to another to satisfy different needs.

One other important concern is to consider the different bulk of the muscles that the person may have in their hands, some people such as slim ladies truly have a very small amount of muscles and tissue in their hands while some men have a very bulky hands and fingers which should not be ignored. Also importantly some people have underlying arthritis that has changed their joint in a way that they are much larger than usual and use of the present gloves is simply difficult for them. Therefore, different size gloves will be introduced to cover this very important issue and need.

Also importantly the surface of the gloves opposing the palmar lines of the joints may have a series of lines of depression to match them and allow an easier function. In some models the area between the joints in front may be made more expanded to match the shape of the fingers a bit.

The sleeves of these gloves in the wrist area may be also made to be adjustable by using a band for tightening the wall of the glove for this reason with snaps, etc., or any other similar techniques or means to allow an adjustable method of closing the sleeves of the gloves, in order to prevent the tightening of the lower arm or wrist area and creating relative ischemia or discomfort of any kind.

The other important concern is about use of these gloves in conditions where there is a possibility of contamination with dangerous or lethal germs such as Hepatitis virus, AIDs virus, etc., which may be acquired by sticking with a contaminated sharp object. The applicant wants to express that the introduction of HIV virus in particular and hepatitis virus and similar germs to a lesser degree has created an extreme concern in the medical field as well as the public. One major consideration during working in a medical field is to prevent being stuck by contaminated needles and/or sharp objects. In this field there are ways way in which this can happen; from giving a shot to a patient or assisting in operation to gathering and cleaning the materials which were used in a procedure, etc. There is a big fear among concerned staff or the health suppliers about the possibility of a medical staff being stuck by a contaminated needle and a sharp object which creates a medical, psychological, medico-legal and economical problems which are very hard to solve. In general there has been no simple solution for this that the inventor knows of. Double gloving has not been an answer when a sharp needle can easily go through the thickness of them when it is forced hard enough or stuck in the right angle. Therefore, the inventor is introducing his idea of using pieces of hard and resistant materials such as plastic, metal or any similar materials that can be used effectively to shield and prevent or at least to diminish this chance. This may be done by having a thin but still a resistant material that will resist and protect against the sharp objects and which will be used in making such gloves. These may be made in the form of a resistant mesh of metal embedded inside the latex layer as well.

In one model of this invention special gloves will be made from latex or similar suitable material that has a series of hard plastic or metal shields shaped properly and placed either inside the glove wall, under its inner surface, on the outside surface or in any part of its thickness or surfaces or over the hands and its vicinity so that this combination functions as a shield to prevent the sharp objects from perforating the whole thickness of this unit. Importantly the nature, the matrix, the material, the number, the position, the size, the shape, the thickness, the length, the width, the coloring, and other important specifics and characteristics of these shields and their make-up may vary from one model to another to satisfy different needs.

Importantly this may be made from a series of bands of steel, metals or any other resistant protective materials that can perform this protection, to be placed in the wall of these gloves to prevent the sharp objects or similar dangerous things from going through it. One particular model of these units is shown in FIG. 6B. In this model a series of a thin bands of steel are placed next to each other perpendicularly to provide protection as well as capacity of motion and being able to be pulled in different ways. The combinations of such materials when embedded inside the latex matrix will be of significant benefit. Importantly the bands of steel may have different shapes, they may be wider in one side and thinner in the other parts, they may be made from series of thinner units with some expansions in some parts, their thickness may vary, they may have some fixed spots related to the other parts, they may have hinges in some areas, and all different shapes and changes are to further decrease the chance of a sharp object from going through it. Also, they may be placed in two or more layers so that the opening of one layer is opposed by the other layer and blocks it effectively. The outer surface of these bands will be made rough or with criss-crossing slightly raised lines to prevent the tip of the sharp object and from slipping and finding a way through the connection sites of these bands. It is true that this may not be totally effective in each and every case, however it still will be beneficial in many cases and at least they will diminish to some degree these accidents. It is also true that this technique will cause some difficulty and may not be used all of the time, however at least it can be used in certain cases. The fact that the presence of the shields will make these units clumsy and less comfortable may be compensated for by incorporation of the other beneficial figures of these units as mentioned above.

In some models these shields will be made in a shape such that their surface has some irregularities and lines to prevent the tip of the needle from slipping and going into the soft wall. The connection in the joint areas will also have a series of overlapping and angulations in the borders with lines in connection lines to prevent from the needles from entering unprotected areas. The place, location, the number and thickness and other characteristics of these shields may vary and they may be placed only in some areas of the gloves and in different uses they may be placed in different places which appear to be more needed or functional. It is possible to place those in only some areas rather than the whole surface of the hands and the idea may be to avoid making a very bulky, difficult to use unit that people simply avoid using. Therefore, it is possible to reach the conclusion that some protection is better than no protection.

Importantly, in some other models, in order to achieve protection, the walls of these gloves may be made from combinations of two or more layers of different materials, so that each one functions differently, with having different resistance, consistencies or strength and other characteristics, etc. For example, one may be an inner, thin elastic layer (such as latex) that will be the main body of the glove which accepts the shape of hands easily and allows easy motions but also this layer will accept and hold patches, pieces or layers of the other materials (such as rubber, metals, insulators of different natures, magnetic materials, different polymers, etc.) which will be chosen for different purposes and protection (and may be placed under, inside or over, or in vicinity of, this layer). So depending on the nature and the need for protection, the nature, shape, size, thickness, coloring and many other important characteristics of these layers may vary. These layers may be chosen to be more than one. An inner soft lining may be also used for better feeling. The other layers may cover only some special areas for special purposes, for example in cases in which the chance of trauma to the rear surface of the hands are remote or unlikely, models in which the rear surface of the gloves are spared from heavy protective coverings will be made. Also importantly when the protective layering is to be thick and heavy, then the front of the joints in the palms may be spared to avoid making them non-functional. Such a model is shown at FIG. 11 in which the protective patches 43, 44, 45, 46 and 47 are covering only some part of the surface of the fingers and the hands in the palm side. In this figure the other protective pieces shown at 48, 49 and 50 will be made to cover the sides of the fingers as well. Importantly the number, the position, the nature, the size, the shape, the thickness, the length, the width, the coloring, and other important specifics and characteristics of these pieces will vary from one model to another to satisfy different needs. A particular model of these gloves will be made to allow some very special jobs to be done from a distance so that the chance of contamination or injury of any kind to be decreased significantly. For example, the model which is shown in FIG. 13 is one such model. In this model, these gloves are made having protective parts in their construction which have extensions in the tip such that it will prevent the fingers from coming directly in contact with those hazardous materials, conditions or environments. For example with use of such a unit someone may pick up hot small stuffs from the surface of a tray without getting burned. Certain chemicals or a sharp object which has many sharp tips, that at least one of which may stick the hands, can be picked up without fear of being poked, etc. Importantly the number, the position, the nature, the size, the shape, the thickness, the length, the width, the coloring, and other important specifics and characteristics of these pieces may vary from one model to another to satisfy different needs. For example, the model shown in FIG. 14 shows a unit with a concave tip. Also importantly, the nature of these units may be altered favorably to satisfy different special needs, for example, the tip of some units may be made to have magnetic power to attract some metal pieces such as needles. (In some cases the shields inside the gloves may also be made to be magnetic to hold some units made from metal easily). This will be of use when a person is cleaning the surgical materials that has contaminated needles scattered in the mixture of many things. Some other models for different uses may be made as well. The materials used in the body of this piece may be different as well, for example, when someone uses these units with heated material, the main body of these pieces or some part of them may be made to be non-conductant to heat, or they may be made to be non-conductant to electricity, etc.

The use of a latex layer with these new gloves is of significant importance and gives a choice of many uses, since it will allow the unit to fit the hands well and to assume the shape very well, and also to allow units inside it, such as protective pieces or materials to be kept next to each other quite nicely and to function well. The bands of steel will be kept next to each other very well also and latex will allow them to be bent easily, overall allowing the making of better units possible. This combination may have many other uses as well, such as in making dresses of a different kind (such as bullet proof jackets), or using them in other units. Again importantly, they may be made from combinations of different layers in which size and nature may vary. Some models of these gloves may have protective shields for the rear surface of the hands as well. Some of such models may have small protective shields (65 and 67) attached to it, over the knuckles or joints in some points 66 and 68, to function as a protective unit but not to interfere with functions of the joint. A particular model may also be made that only protects the palm of the hands. Also importantly in these models, in order to make the wearing of the units easier, the unit may have only bands of elastic that will go around the fingers and the wrist to hold the unit in place, or a series of snaps or spring pieces may be used to allow the units to be held in place easily in the palms, to be put on and removed easily.

Although in this application the improvements are primarily mentioned for medical gloves, in practice these techniques may be also used in making gloves for better use in many different jobs, professions, use at home for house care and even dishwashing, protection from heat and cold, etc., as well. When the gloves are made to be more comfortable and functional and less clumsy, the chance is that more people will use them. This will be much better than having a very heavy, protective, but non-functional glove that people simply avoid using, when the overall trouble of using the gloves exceeds the tolerance of many ordinary people. Making a work glove such that the inner lining or the wall is from latex or similar material with some areas of protective harder material may be a very useful unit over all and this is what the inventor believes can be of great benefit in protecting peoples, hands from many hazards such as germs, chemical, dirt, mechanical, etc. Importantly, a better and more functional glove may prevent work accidents many times, while they will not slow the reactions and functions of the user.

I claim:

1. A glove comprising digit portions into which digits of a person's hand fit and which allow a person's digits to flex, said digit portions being of non-puncture puncture resistant material, and further including a puncture resistant layer disposed on at least one of said non-puncture resistant portions for protecting a person's digit against puncture, said layer comprising plural segments arranged end-to-end in a proximal-distal sense along said digit portion, each segment being transversely concave for substantially conforming to the contour of a respective portion of a person's digit proximal and distal to a joint of a person's digit, wherein at such joint the respective end-to-end arranged puncture resistant segments comprise respective formations that are in mutually overlapping relation laterally across the full extent of the joint and that are shaped such that one formation nests within the other formation to allow flexing of the joint while at the same time presenting across joint an interference to penetration by a puncturing device, in which said other formation comprises a shallow, laterally-extending trough and said one formation comprises a shape for fitting to said trough to allow flexing of said puncture resistant segments.

2. A glove as set forth in claim 1 in which said one formation has a laterally-extending, short margin that is disposed at an angle to extend slightly out of said trough.

3. A glove as set forth in claim 1 in which each segment has short side edge margins disposed at an angle extending away from the segment.

4. A glove as set forth in claim 1 in which said segments are thin metal.

5. A glove as set forth in claim 1 in which both the thumb and one or more of the fingers respectively have such protective layers, and further including a segment or protective layer disposed to protect that region between the base of the thumb and the base of such one or more fingers, said respective segments at the base of the thumb and the base of one or more fingers comprising respective formations that are in mutually overlapping relation and that are shaped such that one nests within the other to allow flexing of the base of the thumb and finger while at the same time presenting an interference to penetration of a puncturing device.

6. A glove as set forth in claim 1 in which said puncture resistant layer is disposed inside of the non-puncture resistant material.

7. A glove as set forth in claim 1 in which said glove has an inside surface that has raised lines to allow better fit of the glove to the hand.

8. A glove as set forth in claim 1 in which said glove has an outside surface that has raised lines to allow better gripping of objects.

\* \* \* \* \*